US00PP37388P2

(12) United States Plant Patent
Hansen

(10) Patent No.: US PP37,388 P2
(45) Date of Patent: Apr. 28, 2026

(54) ***PANICUM* PLANT NAMED 'Switcheroo'**

(50) Latin Name: ***Panicum hybrid* (L.)**
Varietal Denomination: Switcheroo

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,921

(22) Filed: Nov. 13, 2025

(51) Int. Cl.
*A01H 6/46* (2018.01)
*A01H 5/12* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP29,313 P2 * 5/2018 Ault ..... A01H 5/12
Plt./384

* cited by examiner

*Primary Examiner* — Karen M Redden

(57) ABSTRACT

A new and distinct plant of ornamental Hybrid Switch Grass named *Panicum* 'Switcheroo' with narrow upright foliage with variegated yellowish margins. The upright and dense culms produce compact plants that do not lodge. The dense columnar panicles beginning yellowish-chartreuse and becoming tan seed heads that are retained into winter. The new plant is useful in the landscape as a specimen, en masse, or in a container.

2 Drawing Sheets

Latin botanical classification: *Panicum* hybrid (L.).
Variety denomination: 'Switcheroo'.

STATEMENT REGARDING PRIOR DISCLOSURES UNDER 37 CFR 1.77(B)(6)

The first offer for sale of *Panicum* 'Switcheroo' was a private offer to Prides Corner Farm by Walters Gardens, Inc. on Nov. 15, 2024. Walters Gardens, Inc. obtained the plant and all information relating thereto from the inventor. No plants of *Panicum* 'Switcheroo' have been sold in this country or anywhere in the world, nor has any disclosure of the new plant been made more than one year prior to the filing date of this application, and such sale or disclosure within one year was either derived directly or indirectly from the inventor.

BACKGROUND OF THE PLANT

*Panicum* 'Switcheroo', hereinafter also referred to just by the cultivar name 'Switcheroo' and the "new plant" is a new and distinct cultivar of Hybrid Switch Grass.

The new plant originated as a cross by the inventor of the proprietary unnamed hybrid referenced only by the breeder code 17-1 (not patented) as the female or seed parent and the proprietary unnamed hybrid referenced only by the breeder code 17-6 (not patented) as the male or pollen parent at a wholesale perennial nursery in Zeeland, Michigan in the summer of 2017. The seed was collected in the autumn of 2017 and sown the following spring. The individual seedling was initially selected from among many for further observation in the summer and fall of 2019 at which time it was assigned the breeder code 18-3-11 before assigning the new plant a cultivar name.

The new plant has been successfully asexually propagated by division since late fall of 2020 at the same wholesale perennial plant nursery in Zeeland, MI, and found to produce stable and identical plants that maintain the unique characteristics of the original plant. The plant is stable and reproduces true-to-type in successive generations of asexual reproduction.

BRIEF SUMMARY OF THE PLANT

The female parent has more upright foliage with streaked variegation, and the inflorescence narrower and more dense, and the habit is taller. The male parent is slightly taller, with more arching and solid blue-green foliage, and more open panicles.

The nearest comparison varieties known to the inventor are: 'Wood's Variegated' (not patented) and 'Dewey Blue' (not patented).

'Wood's Variegated' is significantly shorter in habit with a unstable green and white variegation of the foliage. 'Dewey Blue' has a taller habit, the foliage is more arching and solid bluish-green, and the panicle broader.

The following traits of *Panicum* 'Switcheroo', in combination, have been repeatedly observed in multiple generations of asexually propagated plants and distinguish the new plant from all other Hybrid Switch Grass plants known to the inventor:

1. Narrow, upright foliage with variegated yellowish margins;
2. Upright and dense culms producing compact plants that do not lodge;
3. Dense columnar panicles begin yellowish-chartreuse and become tan seed heads that are retained into winter.

BRIEF DESCRIPTION OF THE DRAWINGS

The photographs of the new plant demonstrate the overall appearance of a five-year-old plant growing in an outdoor display garden in Zeeland, MI, including the unique traits. The colors are as accurate as reasonably possible with color reproductions. Ambient light spectrum, source, and direction may cause the appearance of minor variation in color.

DETAILED BOTANICAL DESCRIPTION

Figure 1:
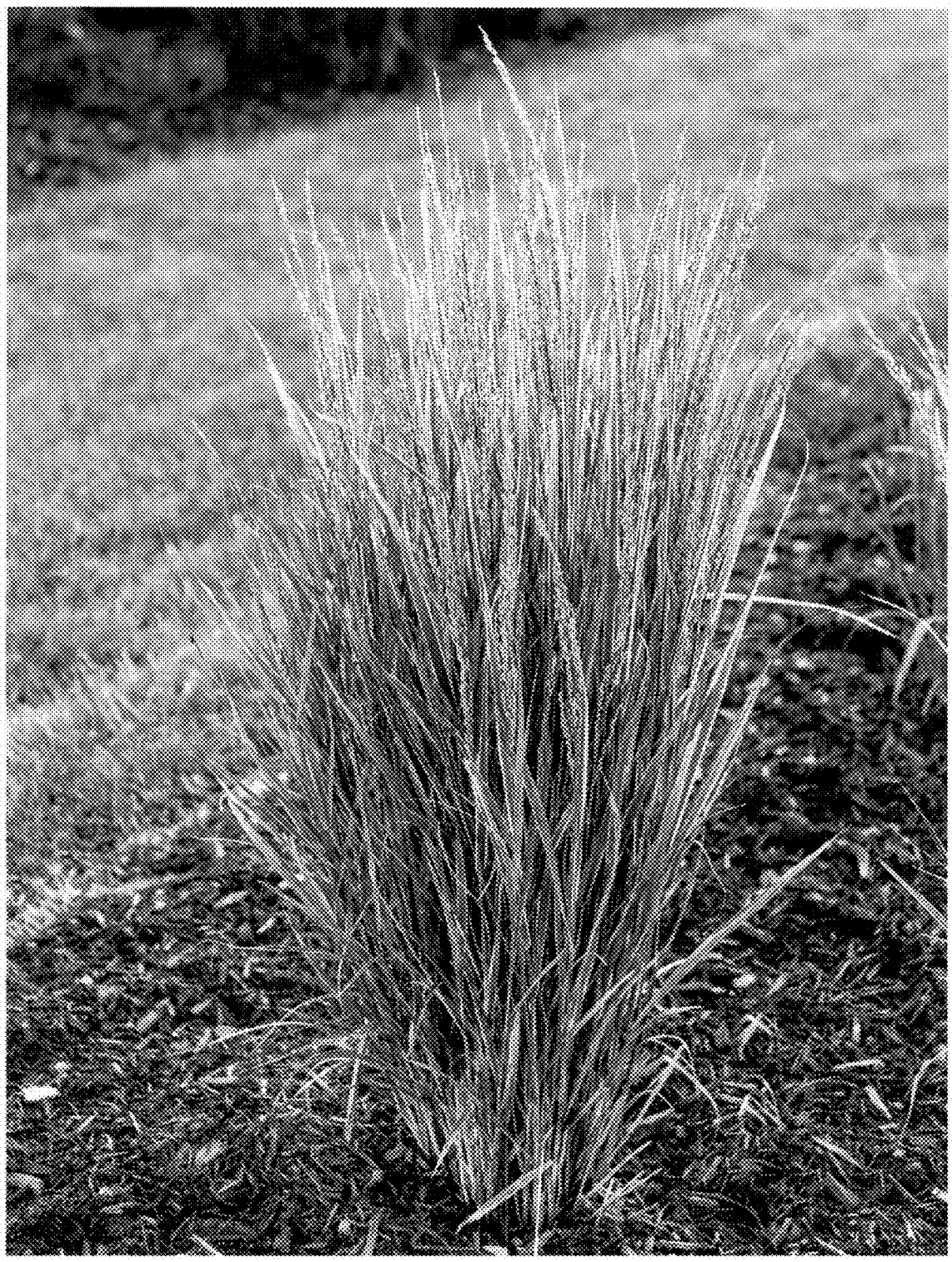
FIG. 1 shows the overall plant in early autumn.
Figure 2:
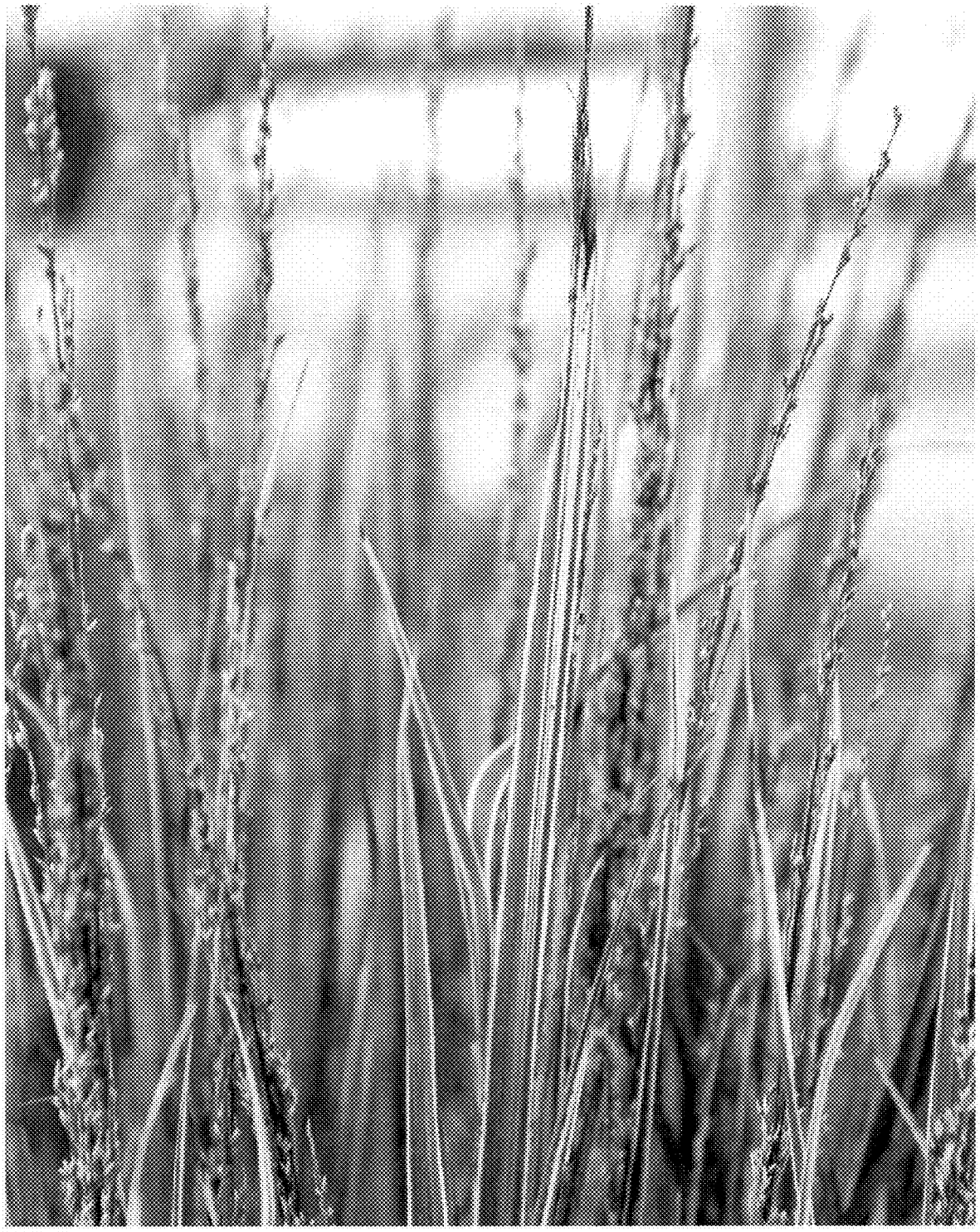
FIG. 2 shows a close-up of the variegated foliage and panicles.

The following descriptions and color references are based on the 2015 edition of The Royal Horticultural Society Colour Chart except where common dictionary terms are used. The new plant, 'Switcheroo', has not been observed in all possible environments. The phenotype may vary slightly with different environmental conditions, such as temperature, light, fertility, moisture, and maturity levels, but without any change in the genotype. The following observations and descriptions are of a five-year-old plant in a loamy-sand trial garden of a wholesale perennial nursery in Zeeland, Michigan, USA, grown in full sun with supplemental water and fertilizer as needed.

Parentage: The female or seed parent is 17-1; the male or pollen parent is 17-6;

Propagation method: By division of the culms;

Time to finish in a 3.8-liter pot: Rapid; about 8 to 10 weeks from 25 mm diameter plug; Rooting habit: normal, coarsely branching; root color nearest RHS 155D;

Plant description:

Plant shape and habit: Hardy herbaceous perennial forming tightly, rhizomatous and upright culms with foliage arching distally, with long dense inflorescences produced near the top of the clump;

Plant size: Foliage height at flowering time is to about 107 cm tall from the soil line to the top of the foliage and 119 cm tall to the top of flowers; about 20 cm wide at the soil line and about 86 cm at the widest point about 70 cm above the soil;

Foliage description: Glabrous; glaucous; linear; flat; margin with microscopic marginal dentations; sheathed from the node of attachment to ligule, except sheath split in distal 5 to 8 cm; adaxial and abaxial surfaces dull; mostly upright with little arching; deciduous but persist through winter; variegated with a lighter margin;

Foliage size: Blade to about 37 cm long, to about 14 mm wide, and sheath to about 16 cm long without sheath; averaging with sheath about 46 cm long and 13 mm wide; shorter at the proximal end; typically 5 leaves per culm; variegated margin to about 3 mm wide at base of blade and continuing down sheath, decreasing toward apex;

Foliage color: Young adaxial margin nearest RHS 8C, adaxial center nearest RHS N138B; young abaxial margin nearest RHS 8C, abaxial center nearest RHS N138B; late summer adaxial margin between RHS 11B and RHS 11C, adaxial center between RHS 189A and RHS N138B; late summer abaxial margin between RHS 11B and RHS 11C and abaxial center between RHS N138A and RHS N137B;

Veins: Parallel; midrib about 0.5 mm across; adaxial slightly recessed, abaxial costate;

Vein color: Adaxial midrib in proximal 4 to 6 cm nearest RHS 194B, abaxial proximal midribs nearest RHS N138B, adaxial and abaxial distal midribs and secondary veins indistinguishable and same color as surrounding leaf;

Ligule: Membranous; with ciliolate margin; to about 2 mm long and about 9 mm across;

Ligule color: Nearest RHS 199D;

Culm: Erect; terete; hollow; glabrous; glaucous; dull surface; about 90% enclosed by leaf sheath; about 150 culms per clump;

Culm dimension: To about 67 cm long without panicle, average about 52 cm; to about 4 mm diameter at base; internode length average about 8.4 cm, shorter proximally;

Culm color: Variable; proximally under sheath between RHS 146D and RHS 145A; where exposed to high light between RHS 137B and RHS 189A;

Node description: About 5 per culm, slightly swollen to about 6 mm diameter;

Node color: Variable; proximally between RHS 199A and RHS 199B, distally nearest RHS 199C;

Inflorescence description: Finely-branched tight panicle, one panicle per culm;

Flower timing: Beginning mid-August, flowering into September, panicles dry and remain effective through winter;

No flower fragrance detected;

Panicle: Cylindrical with acute apex; to about 40.5 cm tall and 3.5 mm across near middle; overall effective color variable, nearest RHS 160A to RHS 147C;

Rachis: Terete, branched, glabrous, glaucous; to about 40.5 cm long and about 3.5 mm diameter at base; branches to about 15 cm long and about 0.7 mm diameter held at nearly 180-degree above horizontal; color nearest RHS N138C;

Spikelet: Usually with two florets; pedicellate; about 14 mm long;

Rachilla: Thin, terete, stiff; to about 18 mm long and about 0.2 mm diameter; color nearest and RHS N138C;

Pedicel: Thin; wiry; cylindrical; glabrous; about 2 mm to 3 mm long and 0.2 mm diameter; color nearest RHS N138C;

Lower glume: Ovate; apex narrowly acute; base truncate clasping; without awn; to about 2 mm long and 1 mm across; color nearest RHS 164D with a faint blush of nearest RHS N186C;

Upper glume: Oblong ovate; apex narrowly acute; base truncate clasping; without awn; to about 4 mm long and 1.5 mm across; color nearest RHS 161D with a faint blush of nearest RHS N186C;

Lemma: Oblong ovate; without awn; acute apex, truncate base; margin entire; upper to about 3 mm long and 1.5 mm across, lower each about 4 mm long and 1.5 mm wide; color nearest RHS 161D;

Palea: Oblong ovate; acute apex, truncate base, margin entire; about 2 mm long and 0.7 mm across; translucent, nearest RHS 160D;

Gynoecium: Two;

*Stigma*.—Two; plumose; protruding about 1.5 mm from glume and about 0.5 mm diameter; color nearest RHS N186A.

*Style*.—Thin; about 1 mm long and 0.1 mm diameter; color nearest RHS NN155A.

*Ovary*.—Ellipsoidal; acute apex, rounded base; about 0.5 mm long and 0.5 mm diameter; color nearest RHS 147D.

Androecium: Three;

*Filaments*.—Short; hair-like; up to 1 mm long and less than 0.1 mm diameter; color nearest RHS NN155D.

*Anthers*.—Three; dorsifixed, longitudinal; about 2 mm long and about 0.7 mm wide; color nearest RHS N186A.

*Pollen*.—Has not yet been observed under present growing conditions.

Fruit: Has not yet been observed;

Hardiness: At least from USDA zone 4 through 9;

Growth: The new plant is very drought once established and the stems are resistant to lodging;

Disease and pest resistance or susceptibility: 'Switcheroo' has not shown rust (*Puccinia* sp.) resistance greater than other *Panicum*. Other disease resistance or susceptibility beyond that typical of other Hybrid Switch Grasses has not been observed.

I claim:

1. A new and distinct cultivar of ornamental Hybrid Switch Grass, *Panicum* plant named 'Switcheroo', as herein described and illustrated.

* * * * *